(12) United States Patent
Rosado-Mendez et al.

(10) Patent No.: US 10,863,968 B2
(45) Date of Patent: Dec. 15, 2020

(54) ULTRASONIC IMAGING SYSTEM WITH ANGULARLY COMPOUNDED ACOUSTIC RADIATION FORCE EXCITATION

(71) Applicant: Wisconsin Alumni Research Foundation, Madison, WI (US)

(72) Inventors: Ivan Miguel Rosado-Mendez, Madison, WI (US); Timothy Jon Hall, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 763 days.

(21) Appl. No.: 14/501,207

(22) Filed: Sep. 30, 2014

(65) Prior Publication Data

US 2016/0089112 A1 Mar. 31, 2016

(51) Int. Cl.
| | |
|---|---|
| *A61B 8/00* | (2006.01) |
| *A61B 8/08* | (2006.01) |
| *B06B 1/02* | (2006.01) |
| *G01S 7/52* | (2006.01) |
| *G01S 15/89* | (2006.01) |
| *G10K 11/34* | (2006.01) |

(52) U.S. Cl.
CPC ............ *A61B 8/4494* (2013.01); *A61B 8/485* (2013.01); *A61B 8/5207* (2013.01); *B06B 1/0215* (2013.01); *G01S 7/52022* (2013.01); *G01S 7/52042* (2013.01); *G01S 7/52047* (2013.01); *G01S 7/52071* (2013.01); *G01S 15/8915* (2013.01); *G01S 15/8927* (2013.01); *G10K 11/346* (2013.01); *G10K 11/348* (2013.01); *B06B 2201/20* (2013.01); *B06B 2201/40* (2013.01); *B06B 2201/55* (2013.01); *B06B 2201/76* (2013.01)

(58) Field of Classification Search
CPC .............. B06B 1/0215; B06B 2201/55; B06B 2201/20; G01S 15/8927; G01S 15/8915; G01S 7/52071; G01S 7/52047; G01S 7/52022; G01S 7/52042; G10K 11/348; G10K 11/346; A61B 8/00; A61B 8/4494; A61B 8/485; A61B 8/5207
See application file for complete search history.

(56) References Cited

U.S. PATENT DOCUMENTS 6,309,356 B1 * 10/2001 Ustuner .............. G01S 7/52026
                                                                            600/443
7,331,926 B2   2/2008 Varghese et al.
(Continued)

OTHER PUBLICATIONS

NJ Kasdin, RJ Vanderbei, MG. Littman, DN Spergel, "Optimal Asymmetric Apodizations and Shaped Pupils for Planet Finding Coronagraphy", 2004, https://arxiv.org/abs/astro-ph/0404388, arXiv:astro-ph/0404388 v1.*

(Continued)

*Primary Examiner* — Serkan Akar
(74) *Attorney, Agent, or Firm* — Boyle Fredrickson S.C.

(57) ABSTRACT

An ultrasound machine for generating push-pulses to excite shear wave stimulation employs separated angled beams that converge at the target region to generate the push-pulses. In one embodiment, the beams are modulated by a set of apodization functions to reduce side lobes caused by the narrowing of the apertures of the beam as well as transducer heating by reducing the average energy deposited in each transducer element.

14 Claims, 3 Drawing Sheets

(56) References Cited

U.S. PATENT DOCUMENTS

| | | | |
|---|---|---|---|
| 7,837,626 B2* | 11/2010 | Chomas | A61B 8/481 600/437 |
| 8,328,726 B2 | 12/2012 | Varghese et al. | |
| 8,727,986 B2 | 5/2014 | Hall et al. | |
| 9,084,559 B2* | 7/2015 | Sumi | A61B 8/08 |
| 9,345,448 B2* | 5/2016 | Fatemi | A61B 8/0858 |
| 2009/0056453 A1* | 3/2009 | McAleavey | A61B 8/08 73/597 |
| 2011/0245678 A1* | 10/2011 | Tamura | A61B 8/08 600/453 |
| 2012/0134233 A1* | 5/2012 | Lin | G01S 7/52022 367/7 |
| 2013/0046175 A1* | 2/2013 | Sumi | A61B 8/08 600/431 |
| 2013/0116561 A1* | 5/2013 | Rothberg | A61B 8/4254 600/438 |
| 2013/0237820 A1* | 9/2013 | Vappou | A61B 8/485 600/438 |
| 2014/0031693 A1* | 1/2014 | Solek | A61B 8/4494 600/447 |
| 2014/0046173 A1* | 2/2014 | Greenleaf | G01N 21/17 600/411 |

OTHER PUBLICATIONS

[RJ Vanderbei, N.J. Kasdin, D.N. Spergel, M. Kuchner, "New pupil masks for high-contrast Imaging", 2003, Proc. SPIE 5170, Techniques and Instrumentation for Detection of Exoplanets, pp. 49-56.*

E.C. Elegbe, M.G. Menon, and S.A. McAleavey, "Comparison of Two Methods for the Generation of Spatially Modulated Ultrasound Radiation Force", 2011, IEEE Trans Ultrason Ferroelectr Freq Control., vol. 58, No. 7, pp. 1344-1354.*

Song et al (Comb-push Ultrasound Shear Elastography (CUSE) with Various Ultrasound Push Beams; IEEE Trans Med Imaging. Aug. 2013 ; 32(8): 1435-1447).*

Inventor: Varghese et al.; Method and Apparatus for Rapid Acquisition of Elasticity Data in Three Dimensions; U.S. Appl. No. 14/276,019; filed May 13, 2014; Whole Document.

* cited by examiner

ULTRASONIC IMAGING SYSTEM WITH ANGULARLY COMPOUNDED ACOUSTIC RADIATION FORCE EXCITATION

STATEMENT REGARDING FEDERALLY SPONSORED RESEARCH OR DEVELOPMENT

This invention was made with government support under HD072077 awarded by the National Institutes of Health. The government has certain rights in the invention.

CROSS REFERENCE TO RELATED APPLICATION

Background of the Invention

The present invention relates to an ultrasonic imaging system providing acoustic radiation force impulse imaging and in particular to a system providing improved tissue discrimination.

Conventional ultrasonic imaging provides visualization of tissue using longitudinal, compressional acoustic waves extending from the ultrasound transducer into the tissue. In standard B-mode imaging, echoes from interfaces between tissues of different acoustic properties are used to develop an image of the tissue outlines.

More recently, ultrasonic imaging has been directed toward the visualization of tissue using transverse, shear waves perpendicular to the direction of ultrasound propagation from the transducer. The shear waves are created by using the ultrasound from the transducer as a "push beam" to apply an acoustic radiation force to the tissue that moves the tissue in a target region producing the shear waves propagating away from the target and perpendicular to the push beam. The propagation of the shear wave is then monitored using longitudinal, compression acoustic waves whose echoes are used to track tissue displacement caused by the shear wave. Measurement of shear wave induced displacements can provide estimates of shear wave speed and shear modulus providing additional insight into tissue properties.

Generally greater movement of the target tissue provides higher signal-to-noise measurements of the resulting shear wave. This greater displacement may be obtained by using a long pulse duration for the acoustic push beam, for example, 100 microseconds for the acoustic push beam versus one microsecond for conventional ultrasound beams. The force of the beam (F) may also be increased by increasing the intensity (I) of the signal according to the formula:

$$F = \frac{2\alpha I}{c} \quad (1)$$

where a is the tissue acoustic attenuation and c is the longitudinal wave propagation speed.

For this reason, the ultrasound transducer is normally excited to focus energy over a section of its surface to the region where shear wave excitation is desired.

SUMMARY OF THE INVENTION

The present inventors have determined that, in tissue with high acoustic attenuation, a conventional focusing of the ultrasound energy to the region of interest results in substantial acoustic force being applied above the intended region. This misapplication of the force not only reduces the energy deposited in the region of interest but may distort the wave front, making difficult to measure shear wave propagation By dividing the ultrasound energy into two separate intersecting beams, improved deposition of energy can be provided at the desired focal region. In one embodiment, the invention also applies a set of varying apodization functions to the separate beams providing improved uniformity and intensity in the focal region.

Specifically then, the present invention provides an ultrasonic imaging system having an ultrasound transducer array providing for independently controllable array elements providing ultrasonic excitation to the adjacent tissue. A transducer controller communicates with the transducer to: (a) provide a signal to the transducer array to generate a net axial push excitation applying an axial acoustic radiation force along an axis extending away from the transducer in a direction of ultrasound propagation during a push time to a target region in tissue receiving ultrasonic energy from the transducer array and (b) receive signals from the transducer array to monitor a lateral propagation of the shear wave substantially perpendicular to the axis following the push time. Significantly, the signal to the transducer array used to generate the push excitation provides at least two ultrasound beams from apertures laterally separated by a region without emitted ultrasound and having propagation axes that are angled to intersect at the target region.

It is thus a feature of at least one embodiment of the invention to improve the deposition of acoustic force in a desired target region. It is another feature of at least one embodiment of the invention to reduce the mean average energy deposited to each element of the active apertures thereby reducing transducer heating.

The ultrasound transducer may be a linear transducer array and array elements at either end of the array are excited by the signal, and array elements between the ends are not excited by the signal.

It is thus a feature of at least one embodiment of the invention to provide a system that may work with standard imaging hardware.

The ultrasound energy of each beam may be unfocused.

It is thus a feature of at least one embodiment of the invention to provide a larger controlled distribution of energy at the focus.

The signal may excite the array elements producing at least two beams with different amplitudes of ultrasonic signal as a function of the array element number according to at least one non-constant apodization function.

It is thus a feature of at least one embodiment of the invention to provide a method of suppressing periodic transversal (or lateral) lobes in the acoustic force at the target region resulting from reduced aperture size.

The apodization functions may alternate between even and odd functions.

It is thus a feature of at least one embodiment of the invention to select apodization functions that provide offset lobes tending to average away periodicity in the target region. It is yet another feature of at least one embodiment of the invention to select apodization functions that serve to reduce the average heat load to the individual transducer elements.

The apodization functions may provide a Slepian sequence.

It is thus a feature of at least one embodiment of the invention to use an apodization function set well adapted to eliminate lobes.

These particular features and advantages may apply to only some embodiments falling within the claims and thus do not define the scope of the invention.

DETAILED DESCRIPTION OF THE PREFERRED EMBODIMENT

Figure 1:
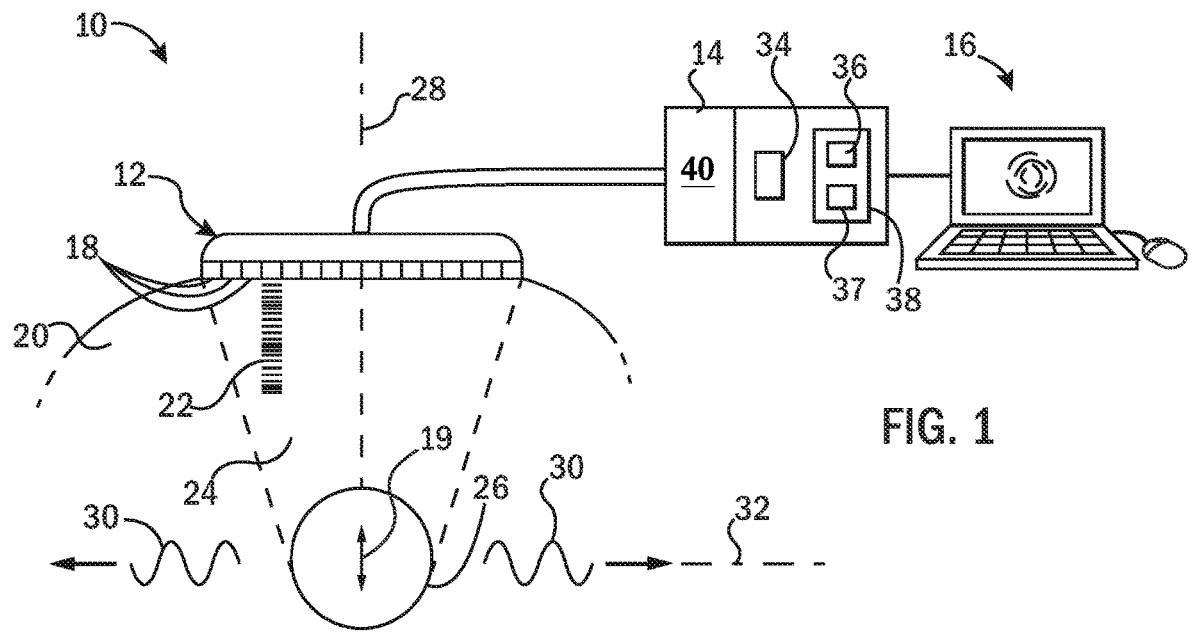
FIG. 1 is a simplified block diagram of an ultrasound machine for providing acoustic radiation force impulse (ARFI) imaging using a one-dimensional linear ultrasound transducer applying ultrasound energy to a focal region to produce shear waves.

Referring now to FIG. 1, an ultrasound machine 10 suitable for use with the present invention provides an ultrasound transducer 12 communicating with a signal processing system 14. The signal processing system 14 may provide for a user interface 16 such as a display terminal and keyboard to receive commands from a user and to provide information derived from ultrasonic measurements to be described.

The ultrasound transducer 12 provides an array of regularly spaced transducer elements 18 that each may convert a received electrical signal into an acoustic signal 22 coupled in the patient tissue 20, for example, through an aqueous gel or the like (not shown). The acoustic signals 22 are generally longitudinal compression ultrasonic signals. The transducer elements 18 are also operated as sensors to receive ultrasonic acoustic energy to produce an electrical signal that may be measured. In this example, the ultrasound transducer 12 may provide for transducer elements 18 arrayed along a single dimension; however, the invention also contemplates the use of a two-dimensional array as will be described below.

Each transducer element 18 may be independently controlled in phase and amplitude so that a beam 24 comprised of multiple ultrasonic signals 22 may be generated and steered by controlling the phases of the constituent ultrasonic signals 22 as is generally understood in the art.

As will be discussed in greater detail below, the signal processing system 14 generally controls the transducer elements 18 to apply ultrasonic signals 22 to the patient 20 to provide a net push-pulse excitation 19 with maximum acoustic force in a target region 26. The force of the push-pulse excitation 19 will be applied generally along a longitudinal axis 28 perpendicular to a contacting face of the ultrasound transducer 12. A result of the push-pulse excitation 19 in the target region 26 will be the production of shear waves 30 having a shear axis generally aligned with longitudinal axis 28 but propagating outward from the target region 26 along transverse axis 32 perpendicular to longitudinal axis 28.

The propagation of the shear waves 30 is measured using the same ultrasound transducer 12, but now applying standard pulse-echo imaging techniques in which an ultrasonic signal is applied to the tissue and an echo or return signal measured to detect tissue displacement associated with the shear waves 30. A succession of such images allows propagation of the shear wave 30 to be measured. These techniques generally detect tissue displacement by spatially correlating speckle and other tissue-specific image features between successive blocks in a stream of successive images as is understood in the art in ARFI imaging.

The signals necessary to produce the push-pulses excitation 19 and to measure the propagation of the shear waves 30 are generated by the signal processing system 14 using a programmed electronic processor 34 executing a stored program 36 contained in a computer memory 38. The resulting data from measurement of the propagation of the shear waves 30 may be stored as image or other data files 37. The processor 34 communicates with interface circuitry 40 which generates the necessary electrical signals at a desired phase and frequency and communicates them to individual transducer elements 18.

Figure 2:
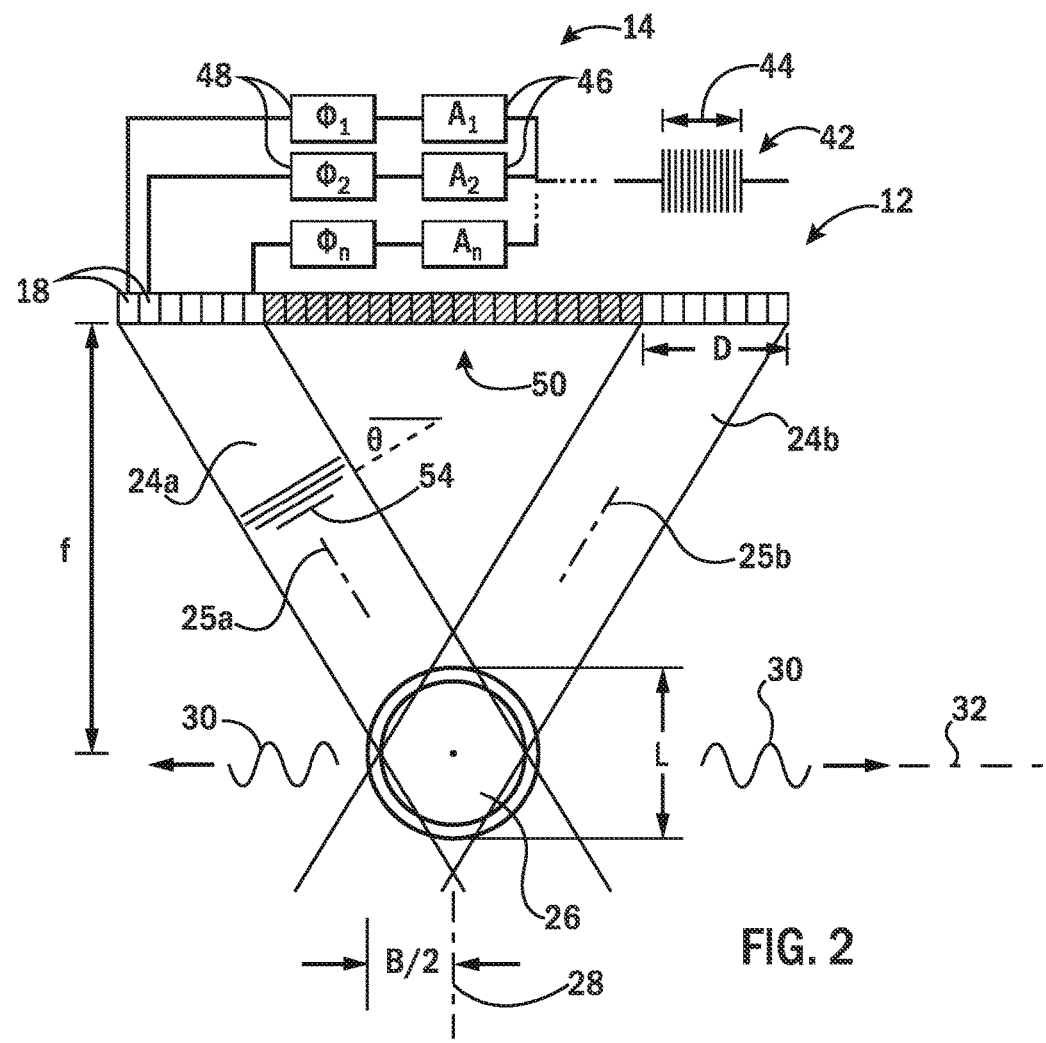
FIG. 2 is a functional block diagram of the activation of the elements of the ultrasound transducer of FIG. 1 per the present invention providing phase and amplitude control of ultrasonic elements in two beam-forming regions.

Referring now to FIG. 2, the signal processing system 14 may generate a base, ultrasonic push-pulse signal 42 having a duration 44 as is required to create the necessary deposition of acoustic force in the target region 26. The duration 44 will be in excess of standard ultrasound pulses used for imaging, for example, greater than 100 microseconds long. This base push-pulse signal 42 may then be separately modulated in amplitude and phase for each of the transducer elements 18, depicted in FIG. 2 by a set of amplitude modulation blocks 46 and phase modulation blocks 48 that may be individually controlled. The amplitude modulation blocks 46 and phase modulation blocks 48 may be implemented entirely in the execution of the program 36 or may employ dedicated hardware components.

Each of the signals after passing through the amplitude modulation blocks 46 and phase modulation blocks 48 may be applied to a subset of the transducer elements 18 to produce two separate ultrasound beams 24a and 24b. These ultrasound beams 24a and 24b propagate along respective propagation axes 25a and 25b angled with respect to the longitudinal axis to intersect at a center of target region 26. As is understood in the art, a propagation axis 25 of a beam 24 describes generally a center line of the propagation of energy of the respective beam 24 and may be controlled by proper phasing of the constituent ultrasonic signals 22 forming the beam 24.

The two beams 24a and 24b may be generated, for example, using only the transducer elements 18 at opposite ends of the ultrasound transducer 12 and leaving the transducer elements 18 at a quiet region 50 inactive. The active sections of the ultrasonic transducer 12 outside of the quiet region 50 are referred to as active apertures. This selected excitation of the transducer elements 18 can be done by setting the amplitude of the signals received by those transducer elements 18 at the quiet region 50 to zero using amplitude modulation blocks 46.

For example, in an ultrasound transducer 12 with 192 transducer elements 18 extending a length of two centimeters, transducer elements 18 only in the first six millimeters and last six millimeters may be excited with a space of un-energized transducer elements 18 of eight millimeters between them. For a three-centimeter focal length as will be discussed below, this provides an f-number of 5 for each of the active apertures. Generally, the quiet region 50 will extend at least one-quarter to one-third of the total length or total number of transducer elements 18 of the ultrasound transducer 12, although other proportions are contemplated by the invention.

Figure 3:
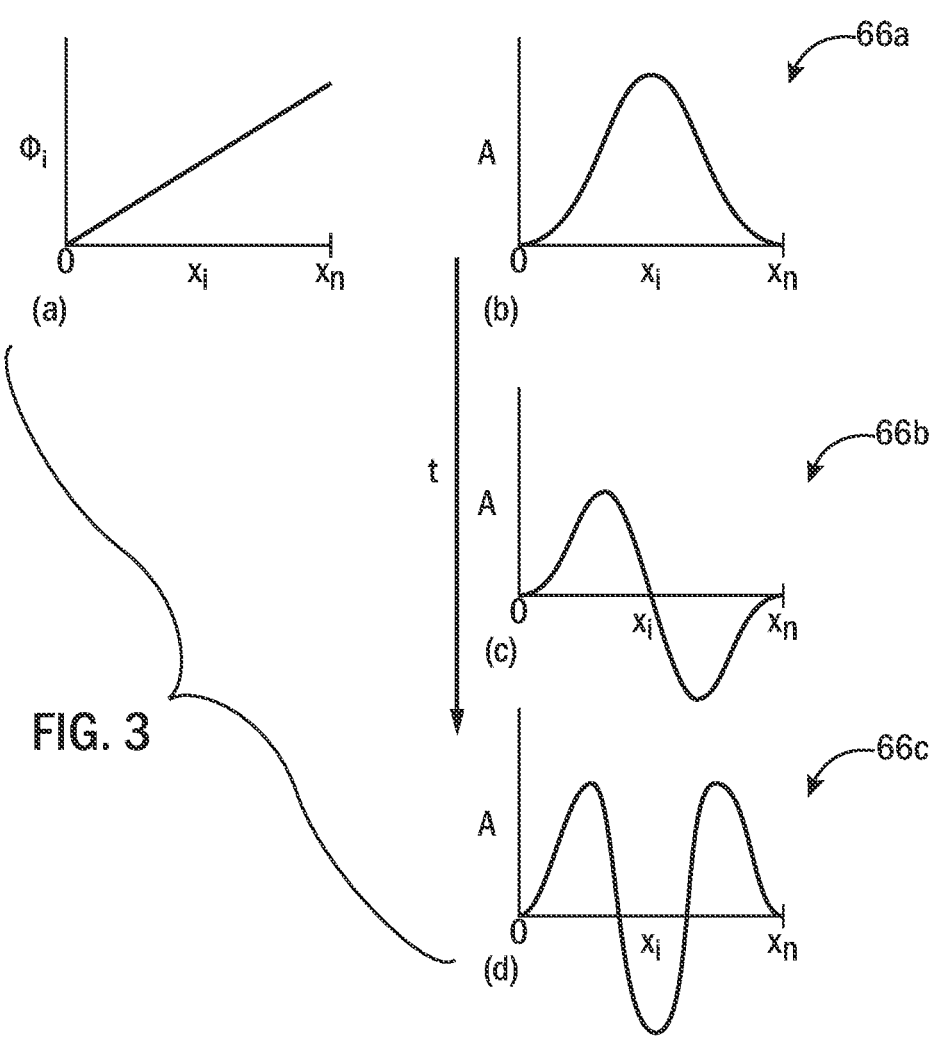
FIG. 3 is four plots of phase and amplitude of the signals applied to the transducer elements to implement a varying apodization function in two unfocused beams.
Figure 4:
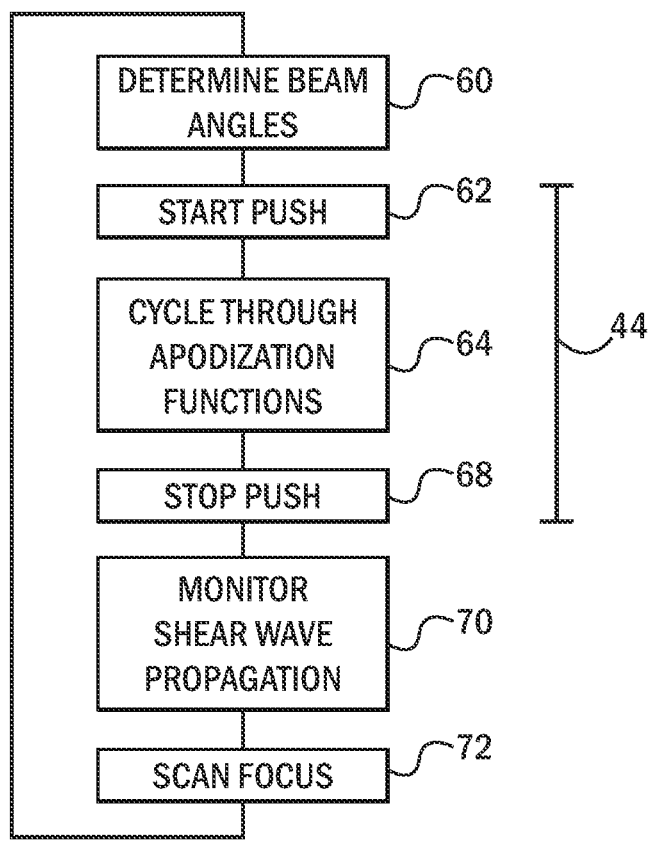
FIG. 4 is a flowchart of the process of the present invention.

The angling of the beams 24a and 24b may be controlled by adjusting the phase φ of the signal of each transducer element 18 using the phase modulation blocks 48 so that the beams' first converge at the target region 26. In unfocused beams 24a and 24b, the phase will be modulated linearly according to the distance $x_i$ of the element number i of transducer from the center of the transducer as shown in FIG. 3, plot (a) to produce a generally planar wavefront 54 at an angle θ with respect to the transverse axis. Thus, in one embodiment, the beams 24a and 24b will generally be angled but not focused. Another embodiment may consider focusing, which requires a nonlinear adjustment of phase across the transducer elements 18. The angle θ and the necessary phasing may be readily computed with knowledge of the desired focal length f being the distance between the center of the ultrasound transducer 12 and a center of the target region 26 along axis 28, and the depth of field L being the height of the target region 26 along the axis 28, the number of transducer elements 18 ($N_e$) in the ultrasound transducer 12 and their pitch (the number of elements per unit length) as follows:

$$\theta = \arctan\left(\frac{N_e \times \text{pitch}}{2} \bigg/ (f + L/2)\right) \quad (2)$$

For example, for an ultrasound transducer 12 with 192 elements, θ=27.23' for f=3 cm and L=1.5 cm.

The phase adjustment may be implemented by time delays $t_i$ applied to the signals of each transducer element 18 as follows:

$$t_i = -\frac{1}{c}|x_i \sin\theta| \quad (3)$$

where i=0 is defined as the edge of the active transducer elements 18 closest to the center of the ultrasound transducer 12.

Generally, the number of transducer elements 18 used for each beam 24a and 24b will be controlled so that the depth of field L, determined geometrically by intersection of the beams 24a and 24b, will be dependent on the width of each beam 24a and 24b and their angle of intersection.

In an alternative embodiment of the invention, beams 24a and 24b may be focused, where the phase of each transducer element 18 will be modulated non-linearly according to the distance of that element (i) to the focus. This provides an equal number of wavelengths of ultrasound between the transducer element and the center of the target region.

Referring now to FIGS. 1, 2, 3 and 4, as indicated by process block 60, the invention first determines beam angles based on desired focal depth f and length of the intersection region L, as discussed above, to determine the necessary phase adjustments of phase modulation blocks 48. A push-pulse signal 42 is then initiated as indicated by process block 62.

The limited spatial extent of each active aperture for the beams 24a and 24b produces transversal side lobes in the deposition of energy within the target region 26 which can be minimized by applying a nonuniform window or apodization function to the signals applied to the transducer elements 18 of each of the beams 24 through the amplitude modulation blocks 46. Further, the relatively short duration of the push-pulse signal 42 compared to the time of flight of the shear waves 30 makes it possible to change the apodization function during the duration 44 of the push-pulse signal 42 as indicated by process block 64.

Referring now to FIG. 3 plots (b)-(d), a set of apodization functions 66a-66c may be generated which each define an amplitude profile of the push-pulse signals 42 delivered to each of the transducers $x_i$ in the active apertures, such that the amplitude of the push-pulse signal 42 provided to each transducer element 18 ($x_i$) is a function of the transverse distance of the transducer element 18 ($x_i$) along the ultrasound transducer 12.

Desirably the apodization functions 66 in the series will generally be orthogonal. One example set of apodization functions 66 provides a Slepian sequence apodization functions—the depicted apodization functions 66a-66c represent the initial three functions in the sequence. In this case, it will be noted that the sequence provides alternate odd and even functions. Each apodization function 66 may be applied for an equal duration within the total duration 44 of tlae push-pulse 19.

An ideal number of apodization functions 66 in the sequence will be 2 NW, where N is the number of transducer elements 18 per beam 24 and W is half the spatial frequency bandwidth outside of which lobes are desirably suppressed. The "space-half bandwidth product" NW may be determined from the design parameters:

$$NW = \frac{DB}{2\lambda_i f} \quad (4)$$

where:

D is the aperture of each beam 24;

B is a lateral width of the target region 26 along the plane through its center;

$\lambda_i$ is a wavelength of the ultrasound; and f is the distance between the center of the target region 26 and a plane of the ultrasound transducer 12.

As an example, for an aperture D of 20 millimeters, a value of B of 10 millimeters, a compression wave of four megahertz in the medium with a propagation sound-speed of 1540 meters per second, and a focal depth f of 30 millimeters, the value of NW is 8.7.

Referring again to FIG. 4, after the full number of 2 NW apodization functions 66 have been applied during the push-pulse signal 42, the push-pulse signal 42 is terminated at process block 68.

It is also important to consider that the oscillatory, odd and even nature of the apodization function activates different parts of each of the active aperture as the sequence of apodization functions is swept. As a result, the average energy (heat load) delivered to each of the transducer elements is reduced. Therefore, this application contributes to reduce transducer heating effects.

Next at process block 70, standard techniques are used to monitor the two shear waves 30 propagating along the transverse axis 32 from the target region 26 in opposite directions. These techniques may include, for example, determining tissue displacement by a comparison of speckle and echogenic tissue structure at successive time intervals to measure the displacement caused by the shear wave.

At process block 72 the focus of the ultrasound transducer 12 may be adjusted to scan the target region 26 to relocate the shear measurements to other measurements within the patient. This process maybe then repeated.

Figure 5:
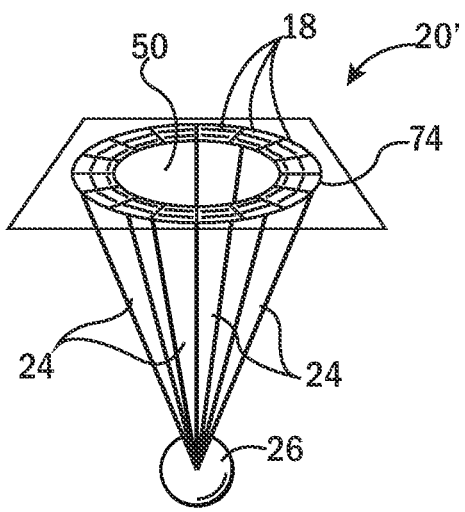
FIG. 5 is a perspective rendering the invention of FIG. 2 expanded to a two-dimensional transducer array or swept one-dimensional transducer array.

Referring now to FIG. 5, it will be appreciated that the above described principles may be extended to a two-dimensional ultrasound transducer 20' in which transducer elements 18 in a ring 74 surrounding a center quiet region 50 may be excited to effectively construct a focused hollow cone of ultrasound energy comprised of multiple separated beams 24 converging at a target region 26. The case depicted in FIG. 5 is simply a geometric rotation of the structure of FIG. 2 about the longitudinal axis 28 bisecting the ultrasound transducer 12 and may be controlled accordingly.

Measurement of the shear wave may be used for a number of purposes including those described in US patent application publication 2010/0222679 entitled: Method and Apparatus for Assessing Risk of Preterm Delivery, assigned to the same assignee as the present invention and hereby incorporated in its entirety.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. An ultrasonic imaging system comprising:
an ultrasound transducer array providing for independently controllable array elements providing ultrasonic excitation to adjacent tissue; and an acoustic radiation force impulse (ARFI) transducer controller communicating with the transducer to:
(a) provide a signal to the transducer array to generate an axial push excitation from a first subset of the array elements applying an axial acoustic radiation force along an axis extending away from the transducer in a direction of ultrasound propagation during a push time depositing the axial acoustic radiation force in a target region in tissue receiving ultrasonic energy from the transducer array, the axial acoustic radiation force adapted to push the tissue into shear wave motion; and
(b) receive signals from the transducer array to monitor a lateral propagation of the shear wave motion perpendicular to the axis following the push time; and
(c) selecting a second subset of the array elements separating the first subset of array elements to be inactive during the entire generation of the axial push excitation wherein at least two ultrasound beams are provided by the axial push excitation and having propagation axes that are angled to intersect at the target region at a depth of the target region within the tissue;
wherein the at least two ultrasound beams first converge at the target region;
wherein the ultrasound beams provide a region without transmitted ultrasonic energy between a center of the ultrasound transducer and the target region;
wherein the ultrasound of each ultrasound beam is unfocused;
wherein the signal excites the array elements producing at least two beams with different amplitudes of ultrasonic signal as a function of the array element number according to at least one non-constant apodization function.

2. The ultrasonic imaging system of claim 1 wherein the ultrasound transducer is a linear transducer array and array elements at either end of the array are excited by the signal, and array elements between the ends are not excited by the signal.

3. The ultrasonic imaging system of claim 1 wherein the ultrasound energy of each beam is phased to provide a planar wavefront at an angle to a front face of the array.

4. The ultrasonic imaging system of claim 1 wherein the apodization function is varied during the push time.

5. The ultrasonic imaging system of claim 4 wherein the apodization functions alternate between even and odd functions.

6. The ultrasonic imaging system of claim 4 wherein the apodization functions provide a Slepian sequence.

7. The ultrasonic imaging system of claim 1 wherein a number of different apodization functions applied during the push time is greater than five.

8. The ultrasonic imaging system of claim 1 further including a display displaying information related to the propagation of the shear waves selected from the group consisting of propagation speed and information derived from propagation speed.

9. The ultrasonic imaging system of claim 1 wherein the total push time is in excess of 10 microseconds.

10. A method of ultrasound imaging employing an ultrasonic imaging system having: an ultrasound transducer array providing for independently controllable array elements providing ultrasonic excitation to adjacent tissue; an acoustic radiation force impulse (ARFI) transducer controller communicating with the transducer to:

(a) provide a signal to the transducer array to generate an axial push excitation from a first subset of array elements applying an axial acoustic radiation force along an axis extending away from the transducer in a direction of ultrasound propagation during a push time depositing the axial acoustic radiation force in a target region in tissue receiving ultrasonic energy from the transducer array, the axial acoustic radiation force adapted to push the tissue into shear wave motion; and (b) receive signals from the transducer array to monitor a lateral propagation of a the shear wave motion perpendicular to the axis following the push time; and (c) select a second subset of the array elements separating the first subset of array elements to be inactive during the entire generation of the axial push excitation;

wherein at least two ultrasound beams are provided by the axial push excitation intersecting at the target region at a depth of the target region within the tissue;

wherein the at least two ultrasound beams first converge at the target region;

wherein the ultrasound beams provide a region without transmitted ultrasonic energy between a center of the ultrasound transducer and the target region;

wherein the ultrasound of each ultrasound beam is unfocused;

wherein the signal excites the array elements producing at least two beams with different amplitudes of ultrasonic signal as a function of the array element number according to at least one non-constant apodization function the method comprising the steps of:

(a) providing the signal to the transducer array to generate the at least two ultrasound beams from the first subset of array elements in the active state emitting ultrasound laterally separated by a region of the second subset of the array elements selected to be inactive during generation of the axial push excitation;

(b) exciting target tissue with axial acoustic radiation force to push the tissue into shear wave motion, the at least two ultrasound beams intersecting at the target region at the depth of the target region within the tissue; and (c) measuring the lateral propagation of the shear wave motion perpendicular to the axis of the ultrasound propagation following the push time.

11. The method of claim 10 wherein the ultrasound energy of each ultrasound beam is phased to provide a planar wavefront at an angle to a front face of the array.

12. The method of claim 10 including the step of varying the apodization function during the push time.

13. The method of claim 12 wherein the apodization functions alternate between even and odd functions during the push time.

14. The method of claim 12 wherein the apodization functions are varied to provide a Slepian sequence.

* * * * *